(12) United States Patent  
Mastenbroek et al.

(10) Patent No.: US 8,729,500 B2  
(45) Date of Patent: May 20, 2014

(54) DIELECTRIC BARRIER DISCHARGE LAMP DEVICE, AND OPTICAL FLUID TREATMENT DEVICE PROVIDED WITH THE DIELECTRIC BARRIER DISCHARGE LAMP DEVICE

(75) Inventors: Olaf Mastenbroek, Goes (NL); Robert Bak, Pila (PL); Jacques Maria Jozef Geboers, Neerpelt (BE); Michiel Van Der Meer, Wouw (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/884,479

(22) PCT Filed: Oct. 25, 2011

(86) PCT No.: PCT/IB2011/054747  
§ 371 (c)(1), (2), (4) Date: May 9, 2013

(87) PCT Pub. No.: WO2012/066440  
PCT Pub. Date: May 24, 2011

(65) Prior Publication Data  
US 2013/0221236 A1   Aug. 29, 2013

(30) Foreign Application Priority Data  
Nov. 16, 2010   (EP) .................................... 10191406

(51) Int. Cl.  
*H01J 65/08* (2006.01)  
*H01J 65/00* (2006.01)  
*H01J 19/57* (2006.01)  
*H01J 5/48* (2006.01)

(52) U.S. Cl.  
CPC . *H01J 65/08* (2013.01); *H01J 5/48* (2013.01); *H01J 19/57* (2013.01)  
USPC .............. 250/455.11; 250/453.11; 250/504 R

(58) Field of Classification Search  
CPC ................. H01J 1/04; H01J 1/05; H01J 1/06; H01J 1/88; H01J 1/90; H01J 1/96; H01J 5/12; H01J 5/20; H01J 5/26; H01J 5/48; H01J 15/02; H01J 15/00; H01J 17/16; H01J 19/57; H01J 65/00; H01J 19/04; H01J 19/08  
See application file for complete search history.

(56) References Cited

U.S. PATENT DOCUMENTS

| 5,386,170 | A | 1/1995 | Kogelschatz |
| 6,087,774 | A * | 7/2000 | Nakayama et al. ........... 313/607 |

(Continued)

FOREIGN PATENT DOCUMENTS

| WO | 2009069015 A1 | 6/2009 |
| WO | 2010079401 A1 | 7/2010 |
| WO | 2011080679 A2 | 7/2011 |

*Primary Examiner* — David A Vanore

(57) ABSTRACT

A dielectric barrier discharge, DBD, lamp device comprises a toroid shaped discharge chamber (10) having a discharge chamber wall (12). The discharge chamber wall comprises a tubular inner wall section (14), a tubular outer wall section (16), and two ring-shaped end wall sections (18, 20). Each of the end wall sections extend between an end of the outer wall section and an end of the inner wall section. A high voltage electrode (22) is provided at an outer surface of the outer wall section of the discharge chamber wall. A low voltage electrode comprises an electrically conducting fluid surrounded by the inner wall section of the discharge chamber wall. The DBD lamp device may be part of an optical fluid treatment device.

18 Claims, 7 Drawing Sheets

(56) References Cited

U.S. PATENT DOCUMENTS

| | | | |
|---|---|---|---|
| 6,592,816 B1* | 7/2003 | Ebel et al. | 422/62 |
| 6,633,109 B2* | 10/2003 | Falkenstein | 313/29 |
| 7,675,237 B2* | 3/2010 | Schiene et al. | 313/607 |
| 7,683,343 B2* | 3/2010 | Schiene et al. | 250/432 R |
| 7,687,997 B2* | 3/2010 | Gaertner et al. | 313/634 |
| 7,820,991 B2* | 10/2010 | Bar et al. | 250/495.1 |
| 7,855,492 B2* | 12/2010 | Schiene et al. | 313/32 |
| 7,990,038 B2* | 8/2011 | Greuel et al. | 313/484 |
| 8,212,478 B2* | 7/2012 | Greuel et al. | 313/607 |
| 8,344,627 B1* | 1/2013 | Hooke et al. | 315/111.21 |
| 8,475,725 B1* | 7/2013 | Antipenko et al. | 422/186.3 |
| 2008/0061667 A1 | 3/2008 | Gaertner | |
| 2008/0093967 A1* | 4/2008 | Schiene et al. | 313/234 |
| 2008/0093971 A1* | 4/2008 | Greuel et al. | 313/484 |
| 2008/0129174 A1* | 6/2008 | Schafer | 313/112 |
| 2008/0185536 A1* | 8/2008 | Schiene et al. | 250/492.1 |
| 2008/0265775 A1 | 10/2008 | Schiene | |
| 2010/0164410 A1* | 7/2010 | Greuel et al. | 315/326 |
| 2010/0253246 A1 | 10/2010 | Hombach | |
| 2011/0266948 A1* | 11/2011 | Kim et al. | 313/578 |
| 2012/0086324 A1* | 4/2012 | Voronov | 313/113 |
| 2012/0205269 A1* | 8/2012 | Ludvig | 206/363 |
| 2012/0237409 A1* | 9/2012 | Greuel et al. | 422/186 |
| 2012/0319576 A1* | 12/2012 | Cseh et al. | 313/579 |
| 2012/0321509 A1* | 12/2012 | Bak | 422/24 |
| 2013/0221236 A1* | 8/2013 | Mastenbroek et al. | 250/435 |
| 2013/0315785 A1* | 11/2013 | Michalik, Richard | 422/119 |

* cited by examiner

DIELECTRIC BARRIER DISCHARGE LAMP DEVICE, AND OPTICAL FLUID TREATMENT DEVICE PROVIDED WITH THE DIELECTRIC BARRIER DISCHARGE LAMP DEVICE

FIELD OF THE INVENTION

The invention relates to the field of dielectric barrier discharge, DBD, lamp devices, and more specifically to a discharge chamber of a DBD lamp device. The invention further relates to an optical fluid treatment device provided with the DBD lamp device of the invention.

An optical fluid treatment device, which may also be referred to as an optical reactor or a photo-reactor, may provide an optical treatment of a fluid, such as sterilization, disinfection, killing or de-activating micro-organisms, oxidation or decomposition of matter by means of light, in particular, but not exclusively, by ultraviolet, UV, light, such as UV-C light.

BACKGROUND OF THE INVENTION

In an optical fluid treatment device, a light source is used to treat a fluid. The light source generates light at an appropriate wavelength, or at different appropriate wavelengths, for a fluid to be treated in a desired manner. The light generated by the light source is supplied to the fluid, which may be stationary or flowing along the light source. The light source may be plunged in the fluid, or may be arranged outside the fluid, and optical means like reflectors may be used to direct the light produced by the light source towards and into the fluid. An example of such an optical fluid treatment device is disclosed in reference WO2010079401.

According to reference WO2010079401, an elongated light source is arranged centrally in a reaction chamber surrounding the light source. A fluid to be treated in the reaction chamber flows around and along the light source.

A disadvantage of the arrangement according to the reference WO2010079401 is its relatively large volume. A further disadvantage results from the measures that need to be taken to ensure that the lamp and the lamp driver housing, which are both in contact with the fluid to be treated, are sufficiently sealed to prevent deterioration of the lamp or the lamp driver due to corrosion or short-circuiting caused by fluid leakage.

SUMMARY OF THE INVENTION

It would be desirable to provide a DBD lamp suitable for fluid treatment in a compact arrangement. It would also be desirable to provide a DBD lamp being less costly. It would further be desirable to provide a fluid treatment device comprising a DBD lamp device and having a robust mechanical design.

To better address one or more of these concerns, in a first aspect of the invention a dielectric barrier discharge, DBD, lamp device is provided, comprising a toroid shaped discharge chamber having a discharge chamber wall. The DBD lamp device comprises a tubular inner wall section, a tubular outer wall section, and two ring-shaped end wall sections, each of the end wall sections extending between an end of the outer wall section and an end of the inner wall section. Such a structure provides a DBD lamp device which opens new possibilities for simple and compact construction of an optical fluid treatment device in which the DBD lamp device is used, by providing the tubular inner wall section of the DBD lamp which may be part of a duct for a fluid to be treated by radiation generated in the DBD lamp.

In an embodiment, the DBD lamp device comprises a high voltage electrode provided at an outer surface of the outer wall section of the discharge chamber wall. This high voltage electrode, which may extend over substantially the outer surface of the outer wall section, can be applied very easily, e.g. by wrapping a sheet of high voltage electrode material around the outer wall section, by sliding a sleeve of high voltage electrode material around the outer wall section, or by winding a wire or strip of high voltage electrode material around the outer wall section of the DBD lamp device.

In an embodiment, the high voltage electrode comprises a wire mesh comprising spaced parallel wires. Upon energizing the high voltage electrode, each of the wires will create local high electric field gradients which promote discharges in the discharge chamber of the DBD lamp device, and an even distribution of discharges in the discharge chamber.

In an embodiment, the high voltage electrode is energized through a conductor at least partly located near or at one of the end wall sections. The conductor, through said arrangement, and upon energizing the high voltage electrode, creates local high electric field gradients at the corresponding end wall section. This will promote a start of the discharge phenomenon in the discharge chamber of the DBD lamp device.

In an embodiment, a low voltage electrode of the DBD lamp device comprises an electrically conducting fluid surrounded by the inner wall section of the discharge chamber wall. When the fluid is contacted at an arbitrary location by a low voltage terminal of a lamp driver, it will act as a low voltage electrode at the inner surface of the inner wall section of the DBD lamp device. The contact location of the low voltage terminal and the fluid may be even outside the area of the inner wall section, e.g. when the inner wall section forms part of a wall of a duct in which the fluid is present, or flows. The lamp driver is adapted to generate a voltage to cause a discharge in the discharge chamber of the DBD lamp device.

In an embodiment, the low voltage electrode formed of the electrically conductive fluid further comprises an electrically conductive element surrounded by the inner wall section of the discharge chamber wall and extending at least partly from a first end of the inner wall section to the other end, and being electrically connected (e.g. to a connection terminal or to a lamp driver) only at the first end. The electrically conductive element, e.g. a metal element or a carbon element, may have an arbitrary design and preferably extends over at least half of the tubular inner wall section between the two tube ends. The electrically conductive element may be formed of a wire which can have a straight form, a spiral form, e.g. touching the wall of the inner wall section, or also any other form. This element may also be formed e.g. by a coating on the inner wall section or by a mesh structure. With this electrically conducting element serving as an electrode the low voltage contact to the electrically conductive fluid is improved.

In an embodiment, the DBD lamp device comprises two bushes, one at or near each end of the inner wall section. The bushes comprise an electrically conductive part, e.g. a metal part, or may be made completely of electrically conductive material like metal. The bushes may e.g. also be formed as plastic or rubber parts with the electrically conductive part such as a ring inside (molded over or sealed with glue/O-ring to the plastic material). The electrically conductive element is electrically connected to one of the two bushes, in particular to the electrically conductive part, and does not touch the electrically conductive part of the second bush. The electrically conductive part of the first bush connecting the electrically conductive element is also connected by a electricity conducting wire to the low voltage output of a driver. The electrically conducting part of the second bush is electrically connected to a measurement input of the driver to be able to measure the conductivity of the fluid between the electrically conductive element and the electrically conductive part of the second bush, i.e. to measure the conductivity of the fluid. With this embodiment a fluid presence sensor is realized using the low voltage electrode. The electrically conductive element is designed to come close to the electrically conductive part of the second bush but can not touch this part of the second bush, i.e. it leaves a gap between its end and the second bush or its electrically conducting part. The gap is dimensioned such that the electrical resistance of the fluid from the end of the electrically conductive element to the electrically conductive part of the second bush can be measured and used to detect the presence of the fluid. This avoids the need to introduce any further fluid detector into the fluid and thus increases maintenance and reliability of the device. The second bush may also be detached for some distance from the end of the lamp e.g. for several cm.

In an embodiment, the discharge chamber wall is made of glass, in particular quartz glass. The type of glass of the different wall sections of the discharge chamber wall may be the same or different. In particular, when the DBD lamp device is to be used in an optical fluid treatment device, i.e. a device for treating fluids by means of light, the inner wall section of the discharge chamber wall is light-transmissive such that radiation generated in the discharge chamber may be radiated into a space surrounded by the inner wall section. Such radiation may then be used to treat a fluid present in, or flowing in or circulate through said space.

In an embodiment, the DBD lamp device comprises a reflective layer provided at an inner surface of the outer wall section of the discharge chamber wall. The reflective layer prevents the radiation generated in the discharge chamber to leave the discharge chamber through the outer wall section, and directs the radiation generated in the discharge chamber to the inner wall section, and to the space surround by the inner wall section. In this way, an amount of radiation in said space is maximized.

In an embodiment, a first luminescent layer is provided at the inner surface of the outer wall section of the discharge chamber wall. A second luminescent layer may be provided at an outer surface of the inner wall section of the discharge chamber wall. The first and the second luminescent layers may generate light at the same wavelength(s) and/or at different wavelength(s) to create an amount and a variety of radiation as desired.

In an embodiment, the DBD lamp device comprises a tubular extension of the inner wall section extending out of the end wall sections. A reflective element or layer is arranged at an outer side of the tubular extension to reflect UV light generated by the lamp towards an optical sensor arranged outside of the tubular extension. This design of the DBD lamp allows the measurement of the UV output of the lamp and of the absorption in the fluid (e.g. water) by measuring the UV light scattered to the corresponding one of the lamp ends and being reflected at the reflective element to a light sensor outside of the lamp. The light sensor may be a direct UV sensor, or a photodiode for visible light, if the reflected UV light is converted to visible light. The conversion may be effected by a phosphor layer arranged between the reflective element and the light sensor. In case of usage of the DBD lamp device to disinfect a fluid with UV-C radiation it is important to be sure that the device is working and that the UV-C output is sufficient to have the required disinfection level. By measuring the UV-C radiation coming out of the inner tube and reflecting this radiation to an appropriate sensor, the measurement of the UV-C output can be achieved in an easy manner.

In a second aspect of the invention, an optical fluid treatment device is provided. The optical fluid treatment device comprises the DBD lamp device as explained above, wherein the inner wall section of the discharge chamber wall forms part of a wall of a duct for a fluid to be irradiated by light generated in the discharge chamber of the DBD lamp device. With the toroid-shaped design of the DBD lamp, a compact structure is obtained, which can be easily integrated in a various fluid treatment applications, varying from low volume flow (i.e. less than 1 liter per minute) to high volume flow domestic, medical or industrial applications. Parts of the DBD lamp at a high electric potential may be remote from, and easily insulated from the fluid in the fluid treatment device, thus providing a compact, robust, low-cost and safe device. Such properties are obtained in the optical fluid treatment device of the invention guiding a fluid to be treated through a duct (reaction chamber) in the DBD lamp, in contrast with WO2010079401 which discloses a fluid to be treated in a reaction chamber to flow around a light source.

In an embodiment of the fluid treatment device of the present invention, the DBD lamp device comprises a lamp driver for generating a discharge in the discharge chamber, and at least part of the lamp driver thermally contacts the duct wall for allowing a heat flow from the lamp driver to the fluid in the duct. Accordingly, cooling of one or more components of the lamp driver can be realized by establishing a heat flow path from the component(s) to the duct or duct wall, such that the heat generated in the component(s) is removed from the device by the fluid absorbing the heat.

In an embodiment of the fluid treatment device of the present invention, a low voltage terminal of the DBD lamp device has a contact surface for electrically contacting a fluid in the duct. The fluid in the duct, provided it is electrically conductive, will function as a low voltage electrode of the DBD lamp, electrically connected to a lamp driver through the low voltage terminal. Accordingly, providing the DBD lamp with a low voltage electrode may be greatly facilitated by using the fluid in the toroid shape of the DBD lamp.

In an embodiment, the fluid treatment device of the present invention comprises a fluid presence sensor for sensing a presence of the fluid in the duct, or in a space in fluid communication with the duct, and the DBD lamp device is activated if a presence of the fluid is sensed by the fluid presence sensor. When the fluid presence sensor indicates that no fluid is present in the duct of the fluid treatment device, or in a space in fluid communication with the duct, there is no fluid to treat by the DBD lamp device, and accordingly, the DBD lamp device need not be activated, e.g. by a lamp driver adapted to supply a voltage to the electrodes of the DBD lamp device to generate a discharge in the discharge chamber of the DBD lamp device. Moreover, if the fluid, in particular the fluid surrounded by the inner wall section of the DBD lamp, is used as a low voltage electrode of the DBD lamp, an absence of fluid in the duct of the fluid treatment device means that no discharge can be generated anyway. Thus, the DBD lamp device needs to be activated only if a presence of the fluid in the duct of the fluid treatment device is sensed. The lamp driver may contain a controller to process a sensing signal from the fluid presence sensor, and to operate the lamp driver according to the sensing signal indicating a presence or an absence of fluid.

In an embodiment, the fluid treatment device of the present invention comprises a fluid flow condition sensor for sensing a flow condition of the fluid in the duct, and the DBD lamp device is activated if a flow condition of the fluid is sensed by the fluid flow condition sensor. In some applications, the DBD lamp device does not need to be activated when a fluid present in a duct is stationary, and only needs to be activated when the fluid is flowing. Examples of such applications are a water tap device connected to a water supply through the fluid treatment device. The water supply may e.g. be part of a public water distribution network, or may be a water container, where the flow of water at an outlet of the duct is controlled by a mechanically operated or electrically operated valve in the duct. A flow condition of the fluid may be sensed directly by a flow sensor in contact with the fluid, or may be sensed indirectly by sensing an open or closed state of a mechanically or electrically operated valve. In the latter case, the fluid flow condition is activated by opening a valve in the duct of the fluid treatment device, the fluid flow condition sensor being coupled to a valve actuator. In the case of a mechanically operated valve, the valve actuator is a knob or lever or similar means, the fluid flow condition sensor sensing a position of the valve actuator. In the case of an electrically operated valve, the valve actuator may be a switch operated by hand or automatically.

In a further aspect of the invention, a fluid reservoir, such as a fluid jug or fluid holder or fluid pitcher or fluid container, is provided, comprising a fluid compartment configured to contain a fluid. The fluid compartment is provided with a fluid discharge opening. The fluid reservoir further comprises the optical fluid treatment device as explained above. The fluid discharge opening of the fluid compartment is connected to the duct of the optical fluid treatment device for fluid to flow from the fluid compartment through the duct when pouring fluid from the fluid reservoir. Thus, when pouring fluid from the fluid reservoir, the fluid is optically treated.

In an embodiment, the fluid reservoir comprises a treatment compartment for housing the DBD lamp device, to keep the main electrical components of the DBD lamp device separated from the fluid.

In an embodiment, a contact surface for electrically contacting a fluid in the duct by the DBD lamp device is located at the fluid discharge opening of the fluid compartment.

In an embodiment, the DBD lamp device of the fluid reservoir comprises a tilting sensor for detecting a tilting angle of the fluid reservoir, and wherein the DBD lamp device is activated when the tilting angle is in a predetermined range. When the fluid reservoir is not used, i.e. when no water is being poured out of the fluid reservoir, the DBD lamp device need not be active, i.e. need not generate light. Therefore, to save energy, which in case of the fluid reservoir may be supplied by a battery, a pouring of fluid from the fluid reservoir is detected by the tilting sensor indicating a use of the fluid reservoir. Only when the tilting of the fluid reservoir, taking into account the arrangement of the duct of the DBD lamp device, is sufficient to create a water flow through the duct, the DBD lamp device is activated. A sufficient tilting may be established when the tilting angle is in the predetermined range. The tilting sensor is an embodiment of a fluid flow condition sensor.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
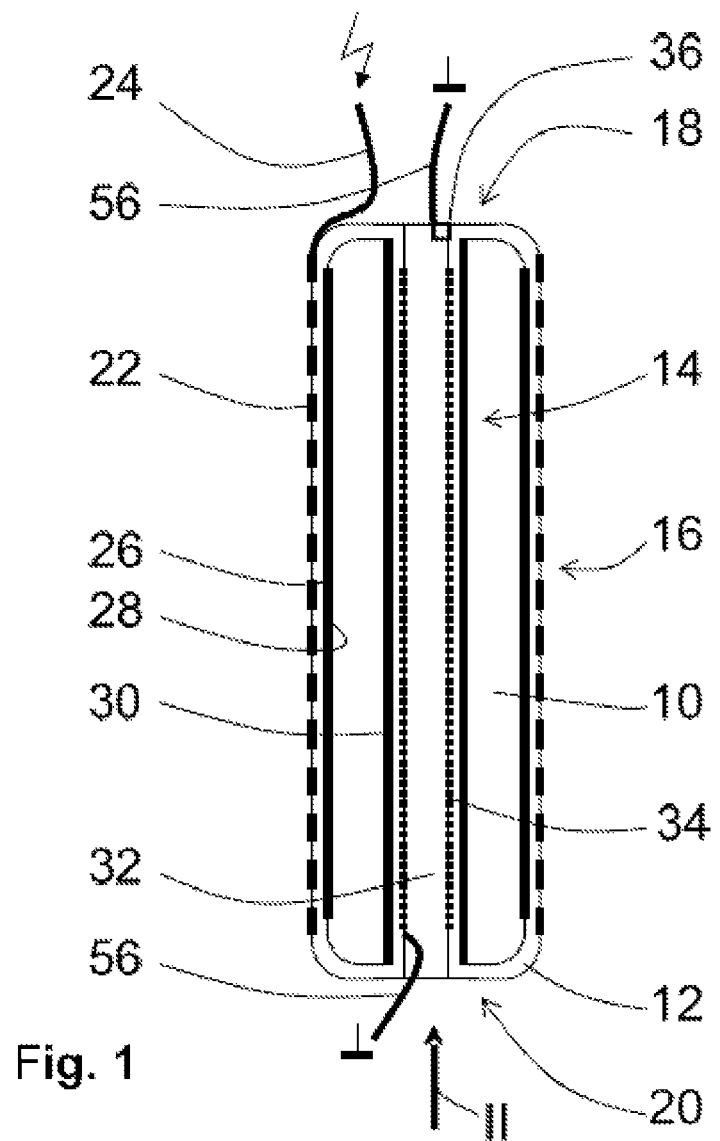
FIG. 1 schematically depicts a cross-section of a part of a DBD lamp device in an embodiment of the present invention.
Figure 2:
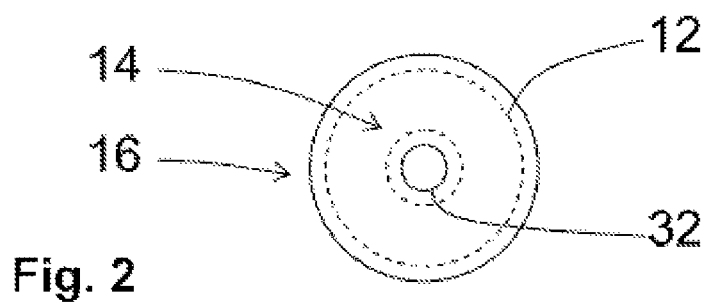
FIG. 2 depicts a view of the embodiment of the DBD lamp device of FIG. 1, as seen in the direction of arrow II in FIG. 1.

FIG. 1 and FIG. 2 depict a part of an embodiment of a dielectric barrier discharge, DBD, lamp device. A discharge chamber 10 is defined by a toroid-shaped discharge chamber wall 12. The discharge chamber wall 12 comprises a generally tubular inner wall section 14 having a length, a generally tubular outer wall section 16 having a length, a first generally ring-shaped end wall section 18 extending between a first end of the outer wall section 16 and the inner wall section 14, and a second generally ring-shaped end wall section 20 extending between a second end of the outer wall section 16, opposite the first end of the outer wall section 16, and the inner wall section 14. In FIG. 1, the lengths of the inner wall section 14 and the outer wall section 16 extend in the direction of arrow II.

In an embodiment, the inner wall section 14, the first and second end wall sections 18, 20, and the outer wall section 16 (and consequently the entire discharge chamber wall 12) are made in one piece.

In an embodiment, the inner wall section 14, the first and second end wall sections 18, 20, and the outer wall section 16 are made from the same material, such as a trans-parent material, e.g. quartz glass.

It is noted that the shapes and dimensions of the different wall sections may vary. A diameter of the inner wall section 14 or the outer wall section 16 may be the same along its length, as illustrated in FIG. 1, or may vary along its length. An outer diameter of the outer wall section 16 may be from about 1 or 1.5 cm to several cm. As shown in FIG. 1, a diameter of the inner wall section 14, or a diameter of the outer wall section 16 is smaller than the length thereof. In other embodiments, a diameter of the inner wall section 14 or the outer wall section 16 may be greater than its length. Further, an end wall section 18 or 20 may have curved edge portions which join with possibly curved end edge portions of the inner wall section 14 or outer wall section 16, as can be seen in FIG. 1 for the end wall sections 18 or 20 and the outer wall section 16. It is further noted that different wall sections may have different thicknesses, either for the whole of each wall section, or locally in one wall section, e.g. to reinforce the discharge chamber wall 12 locally. Also it is noted that FIG. 1 depicts the inner wall section as defining a straight duct, while in other embodiments this duct may be curved. Further, it is noted that the cross-section of the inner wall section 14 and/or the outer wall section 16 may be circular, as depicted in FIG. 2, but may also be e.g. elliptical, oval, or polygonal, with corresponding perimeter shapes of the end wall sections 18, 20.

Referring to FIG. 1, at the outer surface of the outer wall section 16 of the discharge chamber wall 12, a high voltage electrode 22 is provided. As schematically indicated, the high voltage electrode 22 comprises a wire mesh, such as a mesh made by spaced parallel wires extending in a first direction, being woven with, or non-woven with (e.g. laid on, or wound) spaced parallel wires extending in a second direction at an angle different from 0 degrees from the first direction. In a wire mesh constructed in this way, the wires extending in the first and second directions create openings (meshes) between the wires of the first and second direction.

In an embodiment, the wire diameter is between about 0.1 and about 3 mm, e.g. about 0.3 mm. A distance between parallel wires extending in a same direction may be between about 0.5 and about 25 mm.

In an alternative embodiment, the high voltage electrode may comprise a sheet of high voltage electrode material applied to the outer surface of the outer wall section 16. In another alternative embodiment of the high voltage electrode, a pattern of openings may be provided in a sheet of high voltage electrode material applied to the outer surface of the outer wall section 16. The openings may have any shape and surface area, such as a surface area of 1-5 $mm^2$. Instead of applying a sheet of high voltage electrode material, either continuous or provided with a pattern of openings, a coating of high voltage electrode material may be provided on the outer surface of the outer wall section 16, either continuous or provided with a pattern of openings.

The material of the high voltage electrode may be any electrically conducting material, such as a metal, e.g. copper or aluminum, or compounds thereof.

The high voltage electrode is energized, as indicated by the lightning symbol in FIG. 1, through a conductor 24, such as a cable, at least partly located near or at the end wall section 18.

The discharge chamber 10 may comprise a reflective layer 26 provided at an inner surface of the outer wall section 16 of the discharge chamber wall 12. The layer 26 may comprise $Al_2O_3$.

On the reflective layer 26, at its side facing away from an inner surface of the outer wall section 16, and facing the interior of the discharge chamber 10, a first luminescent layer 28 is provided, emitting light when a gas, such as Xe, in the discharge chamber 10 discharges. In an embodiment, the radiation emitted by the first luminescent layer 28 comprises UV-C radiation (wavelength 100-280 nm). The first luminescent layer 28 may contain one or more phosphor compounds, such as $YPO_4Bi$, to stimulate the emission of UV-C light having one or more desired wavelengths.

At an outer surface on the inner wall section 14 of the discharge chamber wall 12, facing the interior of the discharge chamber 10, a second luminescent layer 30 emitting light, e.g. comprising UV-C radiation, when a gas in the discharge chamber 10 discharges, is provided. The second luminescent layer 30 may contain one or more phosphor compounds which may be the same as one(s) in the first luminescent layer 28, or may be different there from.

In a duct 32 defined by an inner surface of the inner wall section 14, a low voltage electrode 34 may be provided, e.g. as a sheet of conductive material or a conductive coating, possibly provided with openings. However, instead of using a low voltage electrode 34, the duct 32 may be filled with a conductive fluid which is contacted at least one point by a low voltage terminal 36, resulting in the conductive fluid, being in contact with the terminal 36, to act as a low voltage electrode.

Said point may e.g. be found at one of, or both ends of the duct 32. The low voltage electrode 34 or low voltage terminal 36 may be connected to mass or ground potential through a conductor 56.

In operation, the low voltage electrode may be kept at mass or ground potential. Upon appropriately energizing the high voltage electrode 22 through the conductor 24, a discharge may develop in the discharge chamber 10. The development of the discharge is promoted by the conductor 24 extending along the end wall section 18, thereby creating local high electric field gradients. Also when applying a wire mesh as a high voltage electrode 22, locally high electric field gradients will develop, facilitating discharges to occur in the discharge chamber 10. The discharges in the discharge chamber 10 will generate UV-C light emission, which will be transformed in UV-C light having a longer wavelength by the luminescent layers 28 and 30. The light is reflected by the reflective layer 26 to be directed essentially to the duct 32. Accordingly, when the inner wall section 14 is light transmissive, the light generated in the discharge chamber 10 by the luminescent layers 28 and 30 will be radiated mainly into the duct 32.

The DBD lamp has a robust mechanical design, which is simple to manufacture, and therefore can be low-cost.

Figure 3:
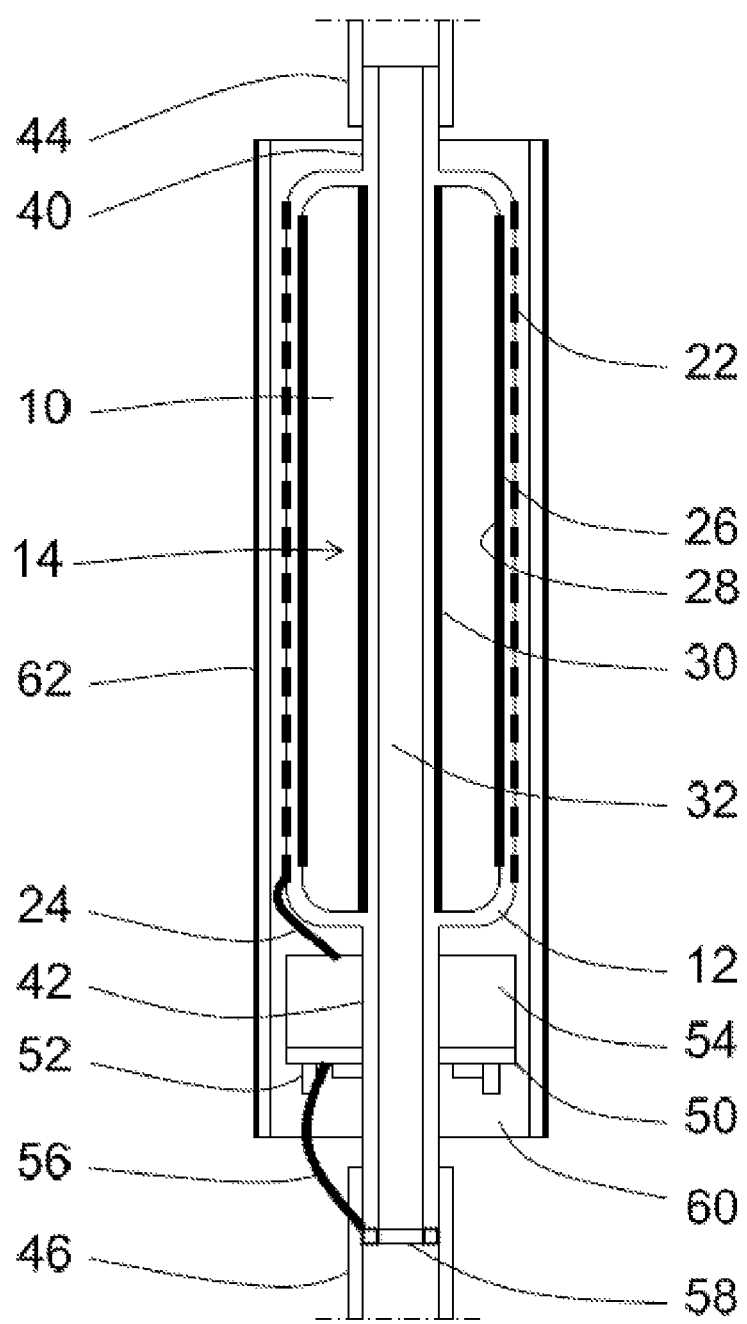
FIG. 3 schematically depicts a cross-section of an optical fluid treatment device including a DBD lamp device in an embodiment of the present invention.

FIG. 3 illustrates an embodiment of an optical fluid treatment device comprising a DBD device as discussed above by reference to FIG. 1 and FIG. 2. In FIG. 3, the same or similar parts, or parts having the same or similar function, have been labeled with the same reference number as in FIG. 1 and FIG. 2.

In FIG. 3, the inner wall section 14 has extensions 40 and 42, respectively, at opposite ends of the inner wall section 14. The extensions 40 and 42 may e.g. be coupled to flexible or rigid fluid ducts 44 and 46, respectively. Thus, a continuous, closed fluid duct is provided in which a fluid may flow from fluid duct 44 through duct 32 to fluid duct 42, or vice versa.

On the extension 42, a lamp driver comprising a printed circuit board, PCB, 50 is provided on which electrical components 52 are mounted for generating a voltage. The lamp driver may be energized by a mains power supply or a battery, or any other electrical power supply (not shown). Further, on the extension 42, the lamp driver may comprise a transformer 54 provided to generate a high voltage, e.g. 4.5 kV, from the voltage generated at the printed circuit board. This high voltage may be applied to the high voltage electrode 22 through the conductor 24. A conductor 56 connects the PCB 50 to a low voltage terminal 58 placed in the fluid duct. The terminal 58 may be a ring made of an electrically conductive material. Thus, an electrically conductive fluid in the fluid duct may act as the low voltage electrode. Instead of a ring, other shapes or configurations of the terminal 58 may be selected, provided they can be in electrical contact with an electrically conductive fluid in the duct 32.

The terminal 58 is shown in FIG. 3 as being placed at an end of extension 42. A further low voltage terminal (not shown) may be placed at the extension 40. With low voltage terminals located both upstream and downstream of the duct 32, this pair of terminals can be used by the lamp driver as a conductivity sensor to establish whether or not an electrically conductive fluid is present in the duct 32, by measuring a conductivity between these terminals. Once the presence of a conducting path (having a conductivity above a predetermined threshold value) between these terminals has been established in the lamp driver, the DBD lamp may be operated. Here, it is noted that when a flow direction of an electrically conductive fluid in the optical fluid treatment device is known, a conductivity sensor at a downstream location relative to the duct 32 will provide a signal representative of the presence or absence of fluid in the duct 32.

With the arrangement of the PCB 50 and the transformer 54 at the extension 42, a heat transfer from the PCB 50 and/or the transformer 54 to the fluid in the fluid duct can be established for cooling one or more of the components 52 and/or the transformer 54, when a thermal contact between the PCB 50 and/or the transformer 54 on the one hand, and the extension 42 on the other hand has been provided for.

When the DBD lamp device comprising the lamp driver and the discharge chamber 10 is energized from a power supply, the light generated in the discharge chamber 10 is received by a fluid present, or flowing, in the duct 32, which fluid is treated thereby to be sterilized or disinfected, to kill or de-activate micro-organisms, or to oxidize or decompose matter in the fluid, to mention some examples. The cubic content of the duct 32, and/or the flow speed of the fluid in the duct 32, and/or the length dimension of the duct 32 (corresponding to the length dimension of the discharge chamber 10) can be designed or selected to obtain a desired residence time of (any part of) the fluid in the duct 32 to obtain a desired fluid treatment effect, while the fluid treatment device is compact, robust and low-cost.

Part of the light generated in the discharge chamber 10 will be received in the inner wall section 14 of the DBD lamp, and through internal reflection will be directed in the longitudinal direction of the inner wall section 14 of the DBD lamp. In the embodiment of FIG. 3, this light will reach the end faces of the extensions 40 and 42 facing away from the DBD lamp, and will have a treatment effect there, thus preventing unwanted growth of organisms at the end faces of the extensions 40 and 42.

Figure 4:
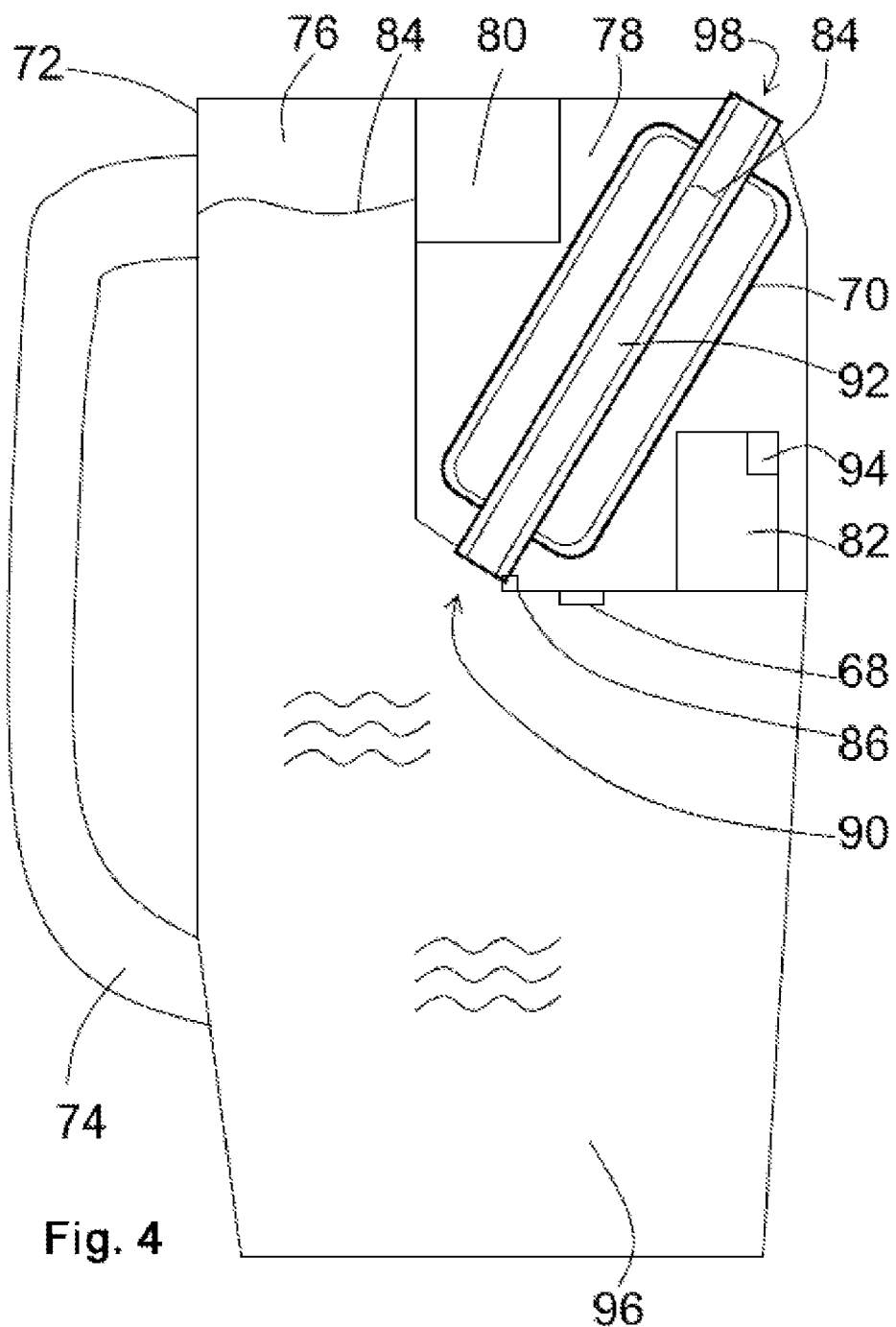
FIG. 4 schematically depicts an embodiment of a fluid reservoir provided with a DBD lamp device of the present invention.

In a practical application, the high voltage electrode and/or the lamp driver may be covered by an insulator 60 to avoid inadvertent electrical contact between a user and operative medium or high voltage DBD lamp device components, and to avoid contamination by dust or fluid and any short-circuiting of DBD lamp device components by such contamination. The insulator 60, such as an insulating sleeve as illustrated in FIG. 3, in particular a heat-shrinkable sleeve, may be provided with a conductive layer 62 or screen at its outer surface to avoid or reduce electromagnetic compatibility, EMC, problems caused by a high frequency operation of the DBD lamp device, in particular EM emission by its high voltage electrode 22. The conductive layer 62 or screen may be connected to mass or ground. As illustrated in FIG. 4, an optical fluid treatment device may be part of a fluid reservoir 72, such as a water jug, having a handle 74 to manually tilt the fluid reservoir 72 to pour fluid 96 from the fluid reservoir 72.

The fluid reservoir 72 comprises a fluid compartment 76, which in the embodiment shown is essentially L-shaped. The fluid compartment 76 may have a filling opening at its upper side, which filling opening may be covered by a cap or lid when no filling of the fluid compartment takes place. The fluid compartment 76 may be open (i.e. enabling passage of fluid) or closed (i.e. not enabling passage of fluid) at its upper side when pouring fluid from the fluid reservoir 72.

The fluid reservoir 72 further comprises a treatment compartment 78 separated from the fluid compartment by a separation wall. The treatment compartment 78 is located at an upper part of the fluid reservoir 72. The treatment compartment 78 houses a schematically represented DBD lamp 70 having a duct 92, a battery 80, and a lamp driver 82. A discharge opening 90 of the fluid compartment 76 adjoins an inlet opening of the duct 92, such that the duct 92 is in fluid communication with the fluid compartment 76. When a fluid 96 is present in the fluid compartment 76, an upper level 84 of the fluid 96 is the same in the fluid compartment 76 and in the duct 92. At the treatment compartment 78, at the inlet opening of the duct 92 (and the discharge opening 90 of the fluid compartment), a contact surface 86 is located which may be in electrical contact with the fluid 96.

To avoid obscuring FIG. 4, some parts of the DBD lamp 70, the battery 80, and the lamp driver 82, as well as insulating structures, and electrical and mechanical connections between them, have been omitted in FIG. 4.

When the fluid reservoir 72 is placed on a horizontal surface, no fluid 96 leaves the fluid jug, and consequently, no fluid 96 needs to be optically treated by the DBD lamp device 70, 82. Accordingly, the DBD lamp device may be inoperative, or at least the DBD lamp 70 may be inoperative. On the other hand, when the fluid reservoir 72 is handled by a user to pour fluid from it, the fluid jug will be tilted to cause fluid 96 to flow from the fluid compartment 76 through the duct 92 to a jug discharge opening 98, and out of the fluid reservoir 72. For the flow of fluid 96 to take place, the fluid reservoir 72 needs to be tilted at least over a predetermined angle. The lamp driver 82 may comprise a tilting sensor 94 to detect a tilting angle of the fluid reservoir 72. When the fluid reservoir 72 has been tilted at least over said predetermined angle, as detected by the tilting sensor 94, the lamp driver 82 activates the DBD lamp 70 to be operative, thereby generating light for treatment of fluid flowing in the duct 92.

It is noted that the light generated by the DBD lamp 70 is guided in the (transmissive) wall of the duct 92 to both ends of the duct 92. The light emerging from the end surfaces of the duct 92 optically treats these parts to keep them clean, in particular clean from micro-organisms and other substances endangering the health of a user of the fluid reservoir.

The contact surface 86 enables the lamp driver 82 to electrically contact the fluid 96, whereby fluid in the duct 92 may serve as a low voltage electrode of the DBD lamp 70.

The treatment compartment 78 may further be provided with a fluid presence sensor, such as a conductivity sensor 68 for measuring a conductivity between two conductivity sensor contacts. The conductivity sensor contacts may be located at a wall part of the treatment compartment 78 facing the fluid compartment 76, such that a fluid contacting both conductivity sensor contacts will allow a controller of the lamp driver 82 coupled to the conductivity sensor 68 to establish the presence or absence of the fluid in the fluid compartment 76. If no presence of fluid in the fluid compartment 76 is established, the DBD lamp 70 need not be activated, even if the tilting sensor 94 would detect a tilting of the fluid reservoir 72.

Figure 5:
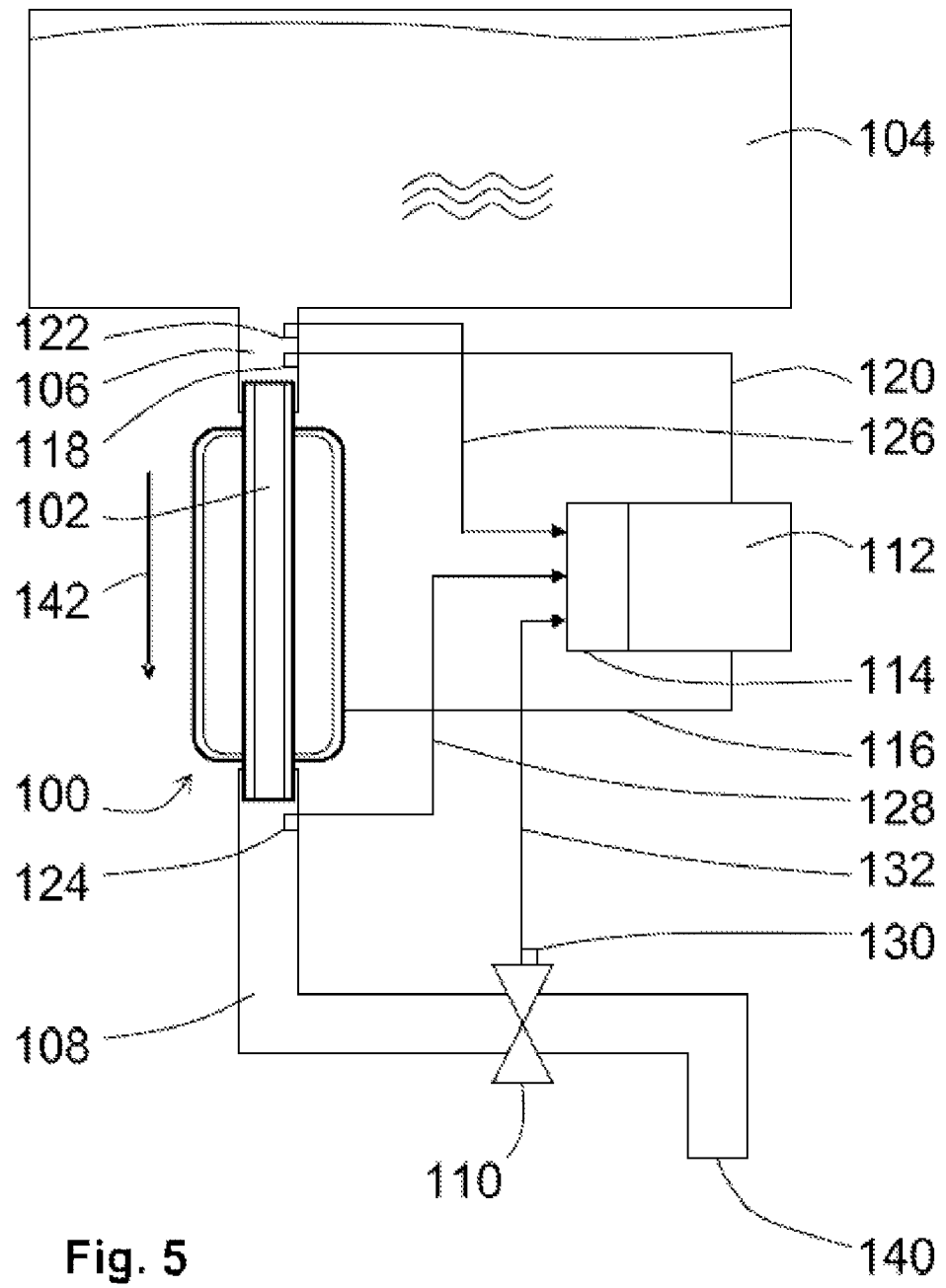
FIG. 5 schematically depicts an embodiment of a fluid supply device provided with a DBD lamp device of the present invention.

FIG. 5 depicts a DBD lamp 100 having a duct 102 coupled between a fluid container or fluid reservoir 104, such as a water reservoir, with a discharge duct 106 on the one hand, and a discharge duct 108 comprising a valve 110 on the other hand. A lamp driver 112 for activating the DBD lamp 100 includes a controller 114. The lamp driver 112 is coupled to a high voltage electrode of the DBD lamp 100 through a line 116, and is coupled to a low voltage terminal 118 through a line 120. A fluid presence sensor comprises a first fluid presence sensor contact 122 and a second fluid presence sensor contact 124, coupled to the controller 114 through lines 126 and 128, respectively. The valve 110 comprises a flow condition sensor 130 coupled to the controller 114 through one or more lines 132.

The low voltage terminal 118 has a contact surface which will electrically contact the fluid so that the fluid in the duct 102 will act as a low voltage electrode of the DBD lamp 100 when the DBD lamp 100 is activated.

The controller 114 is adapted to measure a conductivity between the first and the second fluid presence sensor contacts 122, 124. If the conductivity is above a threshold value, the controller determines that fluid is present between the first and the second fluid presence sensor contacts 122, 124. It is noted here that the first and second fluid presence sensor contacts 122, 124 may also be located both in the discharge duct 106, or both in the discharge duct 108, instead of their locations as shown in FIG. 5.

The controller 114 is further adapted to measure whether the valve 110 is open or closed by the flow condition sensor 130. When the valve 110 is open, fluid may flow from the fluid reservoir 104 to a discharge opening 140 of the discharge duct 108, and in the direction of arrow 142. When the valve 110 is shut, fluid is stationary in the fluid reservoir 104, discharge duct 106, duct 102, and discharge duct 108. Thus, the open state of the valve 110 represents a condition in which fluid flows to the discharge opening 140, whereas the closed state of the valve 110 represents a condition in which fluid does not flow to the discharge opening 140.

The DBD lamp 100 may be activated by the lamp driver 112 when the controller 114 establishes a presence of fluid between the first and second fluid presence sensor contacts 122, 124, and establishes an open state of the valve 110 through the flow condition sensor 130. The flow condition sensor 130 may further be adapted to detect an opening state of the valve 110, i.e. a state of the valve 110 moving from the closed to the open state, but not yet in the open state. In the opening state of the valve 110, the DBD lamp 100 may, as controlled by the controller 114, already be activated by the lamp driver 112 before the fluid starts to flow, in order to have the most effective treatment of the fluid by the radiation generated by the DBD lamp 100.

It is noted that the length of the discharge duct 108 upstream of the valve 110 may be minimized such that the DBD lamp duct 102 practically adjoins the valve 110 to avoid fluid in said length to be stationary for longer times, and not being treated by the DBD lamp 100 when the fluid starts flowing by opening the valve 110.

Figure 6:
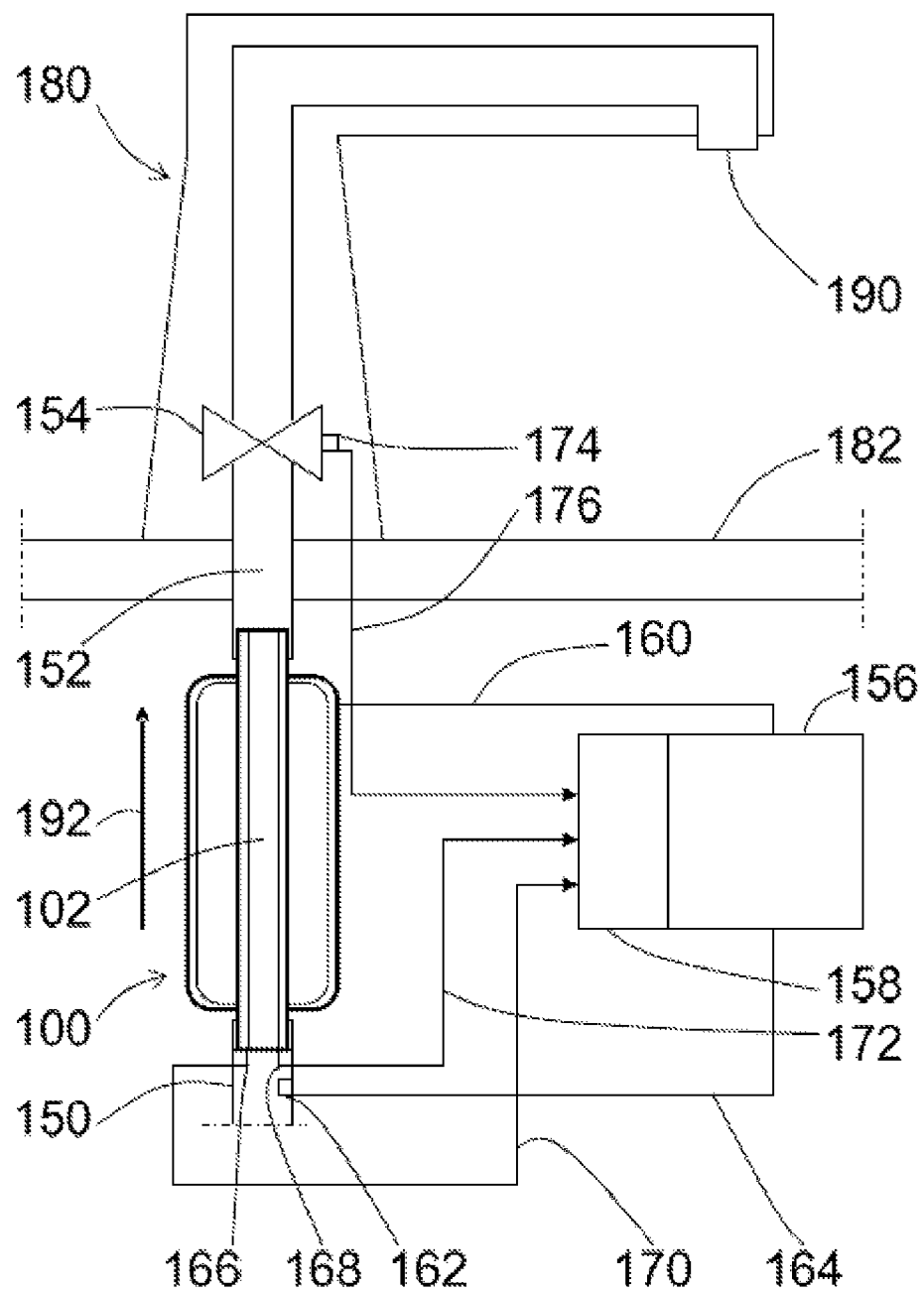
FIG. 6 schematically depicts an embodiment of a water tap device provided with a DBD lamp device of the present invention.

FIG. 6 depicts a DBD lamp 100 having a duct 102 coupled to a fluid supply duct 150 on the one hand, and a discharge duct 152 comprising a valve 154 on the other hand. A lamp driver 156 for activating the DBD lamp 100 includes a controller 158. The lamp driver 156 is coupled to a high voltage electrode of the DBD lamp 100 through a line 160, and is coupled to a low voltage terminal 162 through a line 164. A fluid presence sensor comprises a first fluid presence sensor contact 166 and a second fluid presence sensor contact 168, coupled to the controller 158 through lines 170 and 172, respectively. The valve 154 comprises a flow condition sensor 174 coupled to the controller 158 through one or more lines 176.

The low voltage terminal 162 has a contact surface which will electrically contact the fluid so that the fluid in the duct 102 will act as a low voltage electrode of the DBD lamp 100 when the DBD lamp 100 is activated.

The controller 158 is adapted to measure a conductivity between the first and the second fluid presence sensor contacts 166, 168. If the conductivity is above a threshold value, the controller 158 determines that fluid is present between the first and the second fluid presence sensor contacts 166, 168. It is noted here that the first and second fluid presence sensor contacts 166, 168 may also be located both in the discharge duct 152, or one of the first and second fluid presence sensor contacts 166, 168 may be located in the fluid supply duct 150 and the other one may be located in the discharge duct 152, instead of their locations as shown in FIG. 6.

The discharge duct 152 may be part of a tap 180, such as a water tap, where the valve 154 is operated mechanically (e.g. by a knob or a lever) or electrically (e.g. by activating a switch). The tap 180 may be mounted at a sink on a surface 182. The DBD lamp device is mounted under the surface 182. In a practical embodiment, the DBD lamp device is mounted under or near a kitchen sink, e.g. in a cupboard or other space out of sight of a user of the tap 180.

The controller 158 is further adapted to measure whether the valve 154 is open or closed by the flow condition sensor 174. When the valve 154 is open, fluid may flow from the fluid supply duct 150 to a discharge opening 190 of the discharge duct 152, and in the direction of arrow 192. When the valve 154 is shut, fluid is stationary in the fluid supply duct 150, duct 102, and discharge duct 152. Thus, the open state of the valve 154 represents a condition in which fluid flows to the discharge opening 190, whereas the closed state of the valve 154 represents a condition in which fluid does not flow to the discharge opening 190.

The DBD lamp 100 may be activated by the lamp driver 156 when the controller 158 establishes a presence of fluid between the first and second fluid presence sensor contacts 166, 168, and establishes an open state of the valve 154 through the flow condition sensor 174. The flow condition sensor 174 may further be adapted to detect an opening state of the valve 154, i.e. a state of the valve 154 moving from the closed to the open state, but not yet in the open state. In the opening state of the valve 154, the DBD lamp 100 may, as controlled by the controller 158, already be activated by the lamp driver 156 before the fluid starts to flow, in order to have the most effective treatment of the fluid by the radiation generated by the DBD lamp 100.

Figure 7:
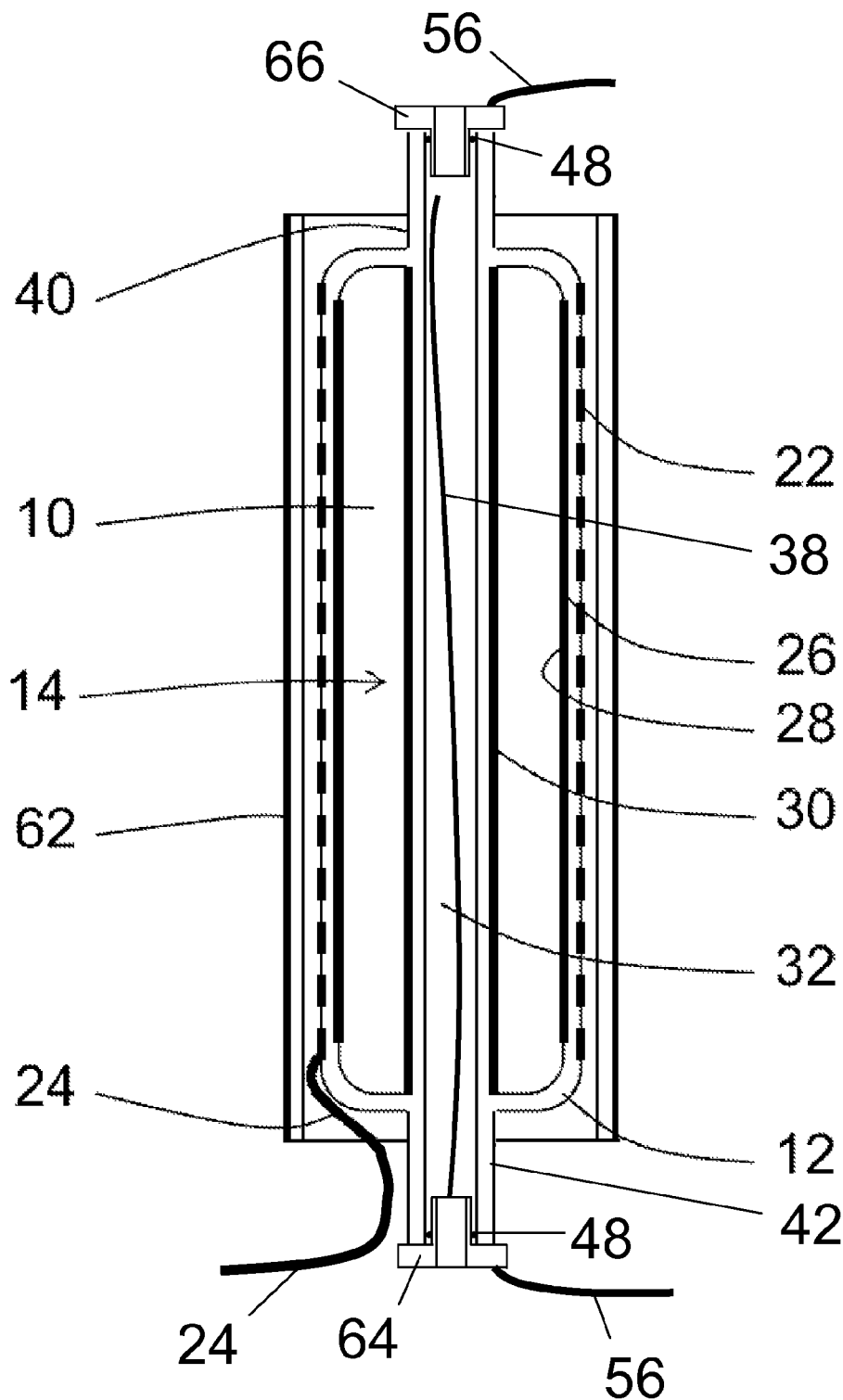
FIG. 7 schematically depicts a cross-section of the DBD lamp device in an embodiment of the present invention.

In FIG. 7, the same or similar parts, or parts having the same or similar function, have been labeled with the same reference number as in FIGS. 1 to 3. The figure shows an embodiment of the DBD lamp device in which the low voltage electrode includes a metal electrode 38 inside the inner tube. The electrically conducting fluid forming the low voltage electrode flow through the inner tube of the lamp. To be able to contact the fluid flowing through the tube in a reliable way, two metallic bushes 64, 66 are provided which are sealed by an O-ring 48 to the ends of the inner tube. The first one 64 of the two bushes is connected by an electrically conducting wire (conductor 56) to the low voltage output of the driver, the second one 66 is connected via a further conductor 56 to a measurement input of the driver to be able to detect the presence of the fluid by measuring the conductivity of the fluid. The metal electrode 38 is connected to the first bush 64 and extends inside the inner tube towards the other tube end. The metal electrode 38 comes very close to the second bush 66 but can not touch the second bush. This design on the one hand allows a better electrical contacting of the fluid flowing in the inner tube, and on the other hand at the same time forms a sensor for detecting the presence of the fluid. The second bush 66 may also be arranged farther away from the inner tube, e.g. up to 10 cm, as far as a measurement of the electrical conductivity of the fluid between the metal wire 56 and the second bush 66 is still possible. For example, a tap may be formed at the end of the inner tube or of extension 42 and the second bush may be arranged at the outlet opening of the tap.

Figure 8:
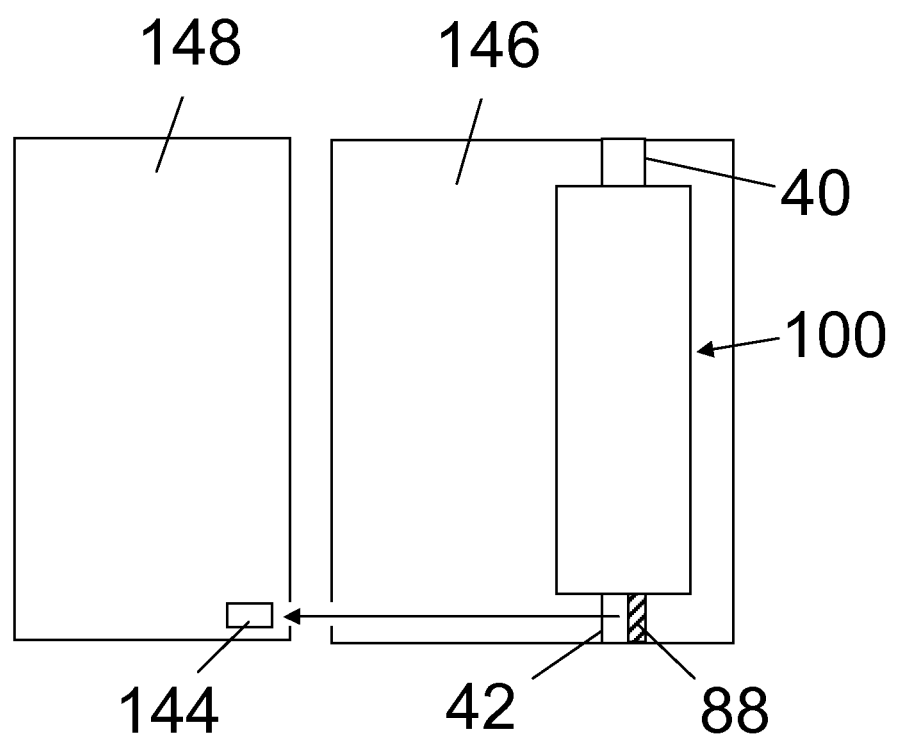
FIG. 8 schematically depicts an embodiment of the DBD lamp device of the present invention which includes a measurement of the UV-C output.

FIG. 8 shows a further embodiment in which the UV-C output of the DBD lamp 100 is measured. The DBD lamp 100 is arranged in a lamp and transformer compartment 146 which is connected to a battery and driver compartment 148. The DBD lamp 100 comprises two extensions 40, 42 on both ends. The UV-C radiation coming out of the inner tube is reflected by a mirror 88 on the outside wall of the inner tube extension 42. The reflected UV-C radiation is travelling through the fluid and then transformed into visible light with a phosphor on the opposite wall of the inner tube extension 42. The visible light is then measured with a light sensor 144. After calibration of this signal when the DBD lamp is still new and with a fluid with known UV-C transmission this signal will be a measurement for both fluid quality and lamp maintenance. This will allow to signal to the user when the performance is too low. As an alternative for the light measurement a direct UV-C measurement (without conversion to light by a phosphor) is also possible but these sensors are less precise and much more expensive. An improved version is a direct measurement of the UV-C passing directly through the reflector of the DBD lamp combined with the above mentioned light measurement at the end of the DBD lamp device. This will improve the accuracy of the system because the DBD lamp device maintenance will be measured independently and only a relative decrease compared to the initial value needs to be measured. The UV-C sensor does not need to be calibrated against a standard in this case.

As explained above, a dielectric barrier discharge, DBD, lamp device comprises a toroid shaped discharge chamber having a discharge chamber wall. The discharge chamber wall comprises a tubular inner wall section, a tubular outer wall section, and two ring-shaped end wall sections. Each of the end wall sections extend between an end of the outer wall section and an end of the inner wall section. A high voltage electrode is provided at an outer surface of the outer wall section of the discharge chamber wall. A low voltage electrode comprises an electrically conducting fluid surrounded by the inner wall section of the discharge chamber wall. The DBD lamp device may be part of an optical fluid treatment device.

It is noted that the DBD lamp may be mounted in any orientation depending on the specific application.

Embodiments of a fluid reservoir or fluid jug or fluid container according to the present invention can be defined according to the following clauses A-D:

A. A fluid reservoir comprising:
  a fluid compartment configured to contain a fluid, the fluid compartment having a fluid discharge opening; and
  an optical fluid treatment device as described above,
wherein the fluid discharge opening of the fluid compartment is connected to the duct of the optical fluid treatment device for fluid to flow from the fluid compartment through the duct when pouring fluid from the fluid reservoir.

B. The fluid reservoir of clause A, further comprising a treatment compartment for housing the DBD lamp device.

C. The fluid reservoir of clause A or B, wherein a contact surface for electrically contacting a fluid in the duct is located at or near the fluid discharge opening of the fluid compartment.

D. The fluid reservoir of any of clauses A-C, wherein the DBD lamp device comprises a tilting sensor for detecting a tilting angle of the fluid reservoir, and wherein the DBD lamp device is activated when the tilting angle is in a predetermined range.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps).

The term "toroid" or "toroid shaped" as used herein, generally refers to an annular shape that is generated by revolving a geometrical figure around an axis external to that figure. In addition, said term as used herein may refer to generally annular shapes having, as further defined herein, an inner wall section and/or outer wall section that may not be circular in cross-section, i.e. in a plane at right angles to said axis, but may be elliptical, oval or polygonal in cross-section.

Any reference signs in the claims should not be construed as limiting the scope of the claims or the invention.

The mere fact that certain measures are recited in mutually different dependent claims does not indicate that a combination of one or more of these measures cannot be used to advantage.

The invention claimed is:

1. A dielectric barrier discharge, DBD, lamp device comprising a toroid shaped discharge chamber having a discharge chamber wall comprising:
  a tubular inner wall section;
  a tubular outer wall section;
  two ring-shaped end wall sections, each of the end wall sections extending between an end of the outer wall section and an end of the inner wall section;
  a low voltage electrode comprising an electrically conducting fluid surrounded by the inner wall section of the discharge chamber wall, the low voltage electrode further comprising an electrically conducting element surrounded by the inner wall section of the discharge chamber wall and extending at least partly from a first end of the inner wall section to the other end, said electrically conducting element being electrically connected only at the first end; and
  two bushes at or near both ends of the inner wall section, said bushes comprising an electrically conductive part, the electrically conductive element being electrically connected to the electrically conductive part of a first one of two bushes without touching the electrically conductive part of the second one.

2. The DBD lamp device of claim 1, comprising a high voltage electrode provided at an outer surface of the outer wall section of the discharge chamber wall.

3. The DBD lamp device of claim 2, wherein the high voltage electrode comprises a wire mesh comprising spaced parallel wires.

4. The DBD lamp device of claim 2, wherein the high voltage electrode is energized through a conductor at least partly located near or at one of the end wall sections.

5. The DBD lamp device of claim 1, wherein the electrically conducting element is a wire or a coating on the inner wall section or a mesh.

6. The DBD lamp device of claim 1, wherein at least one of the two bushes is completely formed of the electrically conductive part.

7. The DBD lamp device of claim 1, comprising a reflective layer provided at an inner surface of the outer wall section of the discharge chamber wall.

8. The DBD lamp device of claim 1, comprising a first luminescent layer provided at the inner surface of the outer wall section of the discharge chamber wall.

9. The DBD lamp device of claim 1, comprising a second luminescent layer provided at an outer surface of the inner wall section of the discharge chamber wall.

10. The DBD lamp device of claim 1, comprising a tubular extension of the inner wall section extending out of the end wall sections, wherein a reflective element or layer is arranged at an outer side of the tubular extension to reflect UV light generated by the lamp towards an optical sensor arranged outside of the tubular extension.

11. An optical fluid treatment device, comprising the DBD lamp device of claim 1, wherein the inner wall section of the discharge chamber wall forms part of a wall of a duct for a fluid to be irradiated by light generated in the discharge chamber of the DBD lamp device.

12. The optical fluid treatment device of claim 11, wherein the DBD lamp device comprises a lamp driver for generating a discharge in the discharge chamber, and wherein at least part of the lamp driver thermally contacts the duct wall for allowing a heat flow from the lamp driver to the fluid in the duct.

13. The optical fluid treatment device of claim 11, wherein a low voltage terminal of the DBD lamp device has a contact surface for electrically contacting a fluid in the duct.

14. The optical fluid treatment device of claim 11, comprising a fluid presence sensor for sensing a presence of the fluid in the duct, or in a space in fluid communication with the duct, and wherein the DBD lamp device is activated if a presence of the fluid is sensed by the fluid presence sensor.

15. The optical fluid treatment device of claim 11, comprising a fluid presence sensor for sensing a presence of the fluid in the duct, the fluid presence sensor being designed to measure a current flow between the electrically conductive element and the electrically conductive part of the second one of the two bushes.

16. The optical fluid treatment device of claim 11, comprising a fluid flow condition sensor for sensing a flow condition of the fluid in the duct, and wherein the DBD lamp device is activated if a flow condition of the fluid is sensed by the fluid flow condition sensor.

17. The optical fluid treatment device of claim 16, wherein the fluid flow condition is activated by opening a valve in the duct, and wherein the fluid flow condition sensor is coupled to a valve actuator.

18. A fluid reservoir comprising:
   a fluid compartment configured to contain a fluid, the fluid compartment having a fluid discharge opening; and
   the optical fluid treatment device of claim 11, wherein the fluid discharge opening of the fluid compartment is connected to the duct of the optical fluid treatment device for fluid to flow from the fluid compartment through the duct when pouring fluid from the fluid reservoir.

* * * * *